United States Patent [19]

Malik et al.

[11] 4,078,143

[45] Mar. 7, 1978

[54] PROCESS FOR DEPOLYMERIZING WASTE ETHYLENE TEREPHTHALATE POLYESTER

[75] Inventors: Abdul-Ilah Malik; Elmer Edwin Most, both of Kinston, N.C.

[73] Assignee: E. I. Du Pont de Nemours and Company, Wilmington, Del.

[21] Appl. No.: 647,995

[22] Filed: Jan. 9, 1976

[51] Int. Cl.[2] .................. C07C 69/82; C07C 67/48; C07C 67/00
[52] U.S. Cl. ..................................... 560/78; 260/2.3; 560/96
[58] Field of Search .............. 260/475 D, 2.3; 560/78, 560/96

[56] References Cited

U.S. PATENT DOCUMENTS

| 3,057,909 | 10/1962 | Sebelist et al. | 260/475 P |
|---|---|---|---|
| 3,830,759 | 8/1974 | Barkley | 260/475 D |
| 3,884,850 | 5/1975 | Ostrowski | 260/475 D |

FOREIGN PATENT DOCUMENTS

| 48-61446 | 8/1973 | Japan | 260/475 D |

*Primary Examiner*—Jane S. Myers

[57] ABSTRACT

Recovery of ethylene terephthalate polymer from waste material is accomplished by glycolysis of the polyester to form bis-(2-hydroxyethyl)terephthalate for repolymerization. Formation of objectionable diethylene glycol is inhibited when glycolysis is accomplished by heating the polyester in a reaction mixture with bis-(2-hydroxyethyl)terephthalate, ethylene glycol and sodium acetate trihydrate, and water is introduced continuously into the reaction mixture during depolymerization of the polyester.

1 Claim, No Drawings

PROCESS FOR DEPOLYMERIZING WASTE ETHYLENE TEREPHTHALATE POLYESTER

BACKGROUND OF THE INVENTION

This invention relates to recovery of polyester from waste material, and is more particularly concerned with inhibiting formation of diethylene glycol during glycolysis of ethylene terephthalate polymers to bis-(2-hydroxyethyl)terephthalate and low molecular weight polyesters thereof.

Production of polyester filaments involves formation of bis-(2-hydroxyethyl)terephthalate, condensation polymerization of this monomer to poly(ethylene terephthalate), melt-spinning into filaments, and winding into packages. The formation of waste occurs during start-up or interruption of various operations, and also results from rejection of non-standard packages. Recovery of polyester waste is an ecological and economic necessity. The problem is complicated by the great variety of products manufactured, which differ in denier and degree of polymerization. There are also differences in the polyester compositions, which include minor amounts of other materials to modify the properties. The polyester may be copolymerized with a minor amount of another compound to provide improvements in crimping, dyeability, flame retardant or anti-static properties of products.

Recovery of polyester waste has been accomplished by glycolysis of the polyester with excess ethylene glycol at elevated temperatures to form bis-(2-hydroxyethyl)terephthalate, and low molecular weight polymers thereof, for recycling in the process indicated above. A continuing problem in the recovery process has been the formation of glycol ethers, principally diethylene glycol. These copolymerize with the bis-(2-hydroxyethyl)terephthalate to form polyester having a reduced melting point and lead to filaments having reduced bulk in filling products, reduced wrinkle resistance and dye lightfastness in textile products, and to variable dyeability in textile products. Other disadvantages are noted in Japanese Patent Publication 48-61446/1973 published Aug. 28, 1973, which discloses the use of tetra-alkyl ammonium hydroxides in the depolymerization process to suppress side reactions.

Barkey U.S. Pat. No. 3,830,759 dated Aug. 20, 1974, discloses that the formation of diethylene glycol is inhibited by the use of lithium acetate dihydrate in combination with zinc acetate dihydrate and/or antimony trioxide. Example 2 illustrates the formation of prepolymer of 0.43 inherent viscosity from dimethyl terephthalate and ethylene glycol. The use of lithium acetate dihydrate resulted in prepolymer having a melting point of 260°–261° C and containing 1.5 mole percent of diethylene glycol. Example 3 illustrates that when recycled ethylene glycol containing 2-4 percent water was used, instead of dry ethylene glycol, the prepolymer had a melting point of 258°–259° C (indicating a higher diethylene glycol content than in Example 1). Example 5 illustrates glycolysis of poly(ethylene terephthalate) scrap to lower molecular weight and subsequent polymerization to form prepolymer. The use of lithium acetate dihydrate in both the depolymerization and repolymerization resulted in prepolymer having a melting point of 253° C and containing 5 mole percent diethylene glycol. The patent discloses at column 7, lines 27-40, that similar experiments in which sodium acetate was substituted for the lithium acetate showed that the results obtained with sodium acetate were not as good.

SUMMARY OF THE INVENTION

The present invention is an improvement in the process of depolymerizing waste ethylene terephthalate polyester by glycolysis of the polyester with excess ethylene glycol at elevated temperatures.

The improvement comprises preparing a reaction mixture of the waste ethylene terephthalate polyester in bis-(2-hydroxyethyl)terephthalate (2G-T monomer), excess ethylene glycol and up to 500 parts per million (ppm) of sodium acetate trihydrate (preferably 200 to 250 ppm), based on the weight of waste polyester, and heating the reaction mixture to depolymerize the waste polyester while continuously introducing water into the reaction mixture to inhibit formation of diethylene glycol. The amount of water introduced per hour may be from about 0.005 to about 0.35 (preferably from 0.01 to 0.03) times the weight of polyester used. The amount of ethylene glycol used for glycolysis is about 0.1 to 0.5 (preferably 0.2 to 0.3) times the weight of polyester used.

DETAILED DESCRIPTION OF THE INVENTION

The process of this invention is suitable for depolymerizing any ethylene terephthalate homopolymer or copolymer in which at least 85 mole percent of the ester units are ethylene terephthalate units. Waste polyester fibers which have a small amount of lubricating spin finish may be used but the waste should otherwise be clean and free of foreign matter.

The bis-(2-hydroxyethyl)terephthalate is used to promote solution of the waste polyester and facilitate its depolymerization. The amount used can be varied over a wide range. Preferably, rapid solution of the polyester will be accomplished by using a weight ratio of bis-(2-hydroxyethyl)terephthalate to waste polyester added of from about 3.1 to about 3.4, but other ratios between 0 and 3.6 can be used.

The amount of ethylene glycol should be sufficient to convert all of the waste polyester to bis-(2-hydroxyethyl)terephthalate. The reaction will proceed more rapidly in the presence of an excess of ethylene glycol but the excess must be removed subsequently and too great an excess will promote formation of diethylene glycol. Hence, it is desirable for the amount of ethylene glycol to be about 0.1 to 0.5 times the weight of the polyester waste used, more preferably 0.2 to 0.3 times the weight of polyester waste used.

An amount of sodium acetate trihydrate may be used ranging up to 500 parts per million, based on the weight of waste polyester used. Preferably the amount is from 200 to 250 parts per million parts of the waste polymer used.

The amount of water used per hour will depend upon the conditions used and can vary from about 0.005 to about 0.35 (preferably from 0.01 to 0.03) times the weight of polyester waste. It can be introduced beneath the surface of the reaction mixture in an inert gas. In a continuous process the water is preferably introduced in combination with the ethylene glycol.

The glycolysis is carried out at an elevated temperature which will provide a rapid depolymeriation of the polyester waste without causing an objectionable amount of diethylene glycol formation. Generally, temperatures from about 200° to about 240° C may be used. Temperatures of 225° to 235° C are preferred.

The process is preferably operated in a continuous manner. For example, a continuous process can be used to treat from about 1400 to about 4300 kilograms of waste poly(ethylene terephthalate) per hour and utilize from about 350 to about 1100 kilograms per hour of ethylene glycol containing from about 2 to about 20 percent water, by weight, based on the weight of the ethylene glycol. The continuous process may be operated at a temperature of 225° C to 235° C at a hold-up time of from about 4 to about 15 hours, where the hold-up time is the time elapsed from the time the ethylene glycol is added to the time the glycolysis is completed.

In the following examples, all percentages are by weight, based on the weight of the waste polyester unless indicated otherwise.

EXAMPLE 1

The following example illustrates the use of water and sodium acetate in inhibiting the formation of diethylene glycol during the glycolysis of waste polyester having polyester molecules that contain aromatic sulfonate groups.

Six runs are made in a stainless steel reactor. The reactor is equipped with a heating mantle, a charging port, a condenser for removing ethylene glycol, an inert gas inlet, and a sampling valve for removing small portions of the reaction mixture.

The reactor is purged of air with inert gas (14% $CO_2$, 86% $N_2$) and a slow flow of the gas is maintained throughout each run. When water is being added to the reaction mass, the gas inlet extends below the surface of the liquid in the reactor, otherwise it is above the surface of the liquid. Water is added starting immediately after the reactor is charged, by passing the gas through a bottle of boiling water and injecting the wet gas into the reactor. The amount of water used is expressed in grams per hour and is an average value calculated from the amount of water lost from the bottle and the time period over which the loss occurred.

The reactor is charged with 400 grams of bis-(2-hydroxyethyl)terephthalate (2G-T monomer), 136 grams of ethylene glycol and sodium acetate trihydrate (NAOAc·3H$_2$O). In one half of the runs 0.035 grams of sodium acetate trihydrate are used and in the other half 0.225 grams are used. The temperature of the charge is raised to a temperature between 190° C and 200° C in 1 hour and then 454 grams of waste polyester are added. The waste polyester consists of polyester fibers which contain, on the average, about 0.5% spin finish with 22 percent of the waste being of an ethylene terephthalate copolyester containing 2 mole percent of ester units arising from the use of sodium 3,5-di(carbomethoxy)-benzenesulfonate. The temperature of the liquid in the reactor is then raised over a period of 1.25 hours to glycolize the polyester. In four of the runs, the temperature is raised to 225° C and in the remaining 2 runs to 235° C; and in half of the runs at each temperature, water is added. Following the glycolysis period, unreacted ethylene glycol is removed over a period of 4.75 hours. At intervals following the time the waste polyester is charged to the reactor, 130 gram samples are removed and analyzed for diethylene glycol content. Results obtained are shown in Table I.

TABLE I

| Run | Temp., ° C | NaOAc . 3H$_2$O ppm* | Rate of Water Addn., gms/hr | Diethylene Glycol Formation Rate mole % /hour** |
|---|---|---|---|---|
| 1 | 225 | 35 | 0 | 0.25 |
| 2 | 225 | 225 | 0 | 0.14 |
| 3 | 225 | 35 | 21.4 | 0.15 |
| 4 | 225 | 225 | 21.4 | 0.08 |
| 5 | 235 | 35 | 0 | 0.35 |
| 6 | 235 | 225 | 21.4 | 0.19 |

*Based on weight of 2G-T monomers produced.
**Average rate of formation after polyester is added.

EXAMPLE 2

The following example illustrates the use of water alone (no sodium acetate) in inhibiting the formation of diethylene glycol during glycolysis of waste polyester.

The process is operated continuously. Polyester waste is added to a reactor at a rate which provides a hold-up time of about 7 hours. In the first two runs the waste is poly(ethylene terephthalate). In Runs 3 and 4 the waste is ethylene terephthalate polymer containing about 0.25 mole percent of copolymerized sodium 3,5-di(carbomethoxy)benzenesulfonate (SSI). Ethylene glycol is added at a rate of 0.25 times the weight of polyester waste. Water is added in combination with the glycol in Runs 2 and 4; no water is added in Runs 1 and 3. The reaction mixture contains an amount of bis-(2-hydroxyethyl)terephthalate which is about 3.25 times the weight of polyester being depolymerized, and is maintained at 235° C. Results obtained are shown in Table II.

TABLE II

| Run | Mole % SSI in waste | Water Added, % of waste | Diethylene Glycol, Mole % in polymer |
|---|---|---|---|
| 1 | 0 | 0 | 2.8 – 3.3 |
| 2 | 0 | 1.0 | 1.7 – 1.8 |
| 3 | ~0.25 | 0 | 6.0 – 7.0 |
| 4 | ~0.25 | 2.5 | 6.0 – 6.5 |

Diethylene Glycol Analysis

Diethylene glycol in polymer (and monomer) is determined by displacing it from the ester groups by heating with 2-aminoethanol containing benzyl alcohol as an internal standard and then analyzing with a gas chromatograph calibrated against standards of known composition. The ratio between the areas of the diethylene glycol and benzyl alcohol peaks is used to calculate the mole percent.

A 1.00 gram sample is placed in a 25 ml round-bottom flask with 2.00 ml of a 2-aminoethanol solution containing 3.24 mg of benzyl alcohol. The flask is fitted with an upright, water-cooled condenser and heated at gentle reflux for 20 minutes. The flask and condenser is removed from the heat. As soon as the boiling stops, 10 ml of 2-propanol is added with shaking, using the propanol to wash down the inside of the condenser. The flask is allowed to cool to room temperature, the condenser is removed and the flask is stoppered tightly. The flask is shaken vigorously and a 3 ml sample is transferred to a gas chromatograph.

A Varian 2860 or 2100 gas chromatograph is used for analysis. The injector and the detector are set at 280°–300° C. The helium flow rate is set at about 20 ml/minute to give times for benzyl alcohol and diethylene glycol around 150 and 190 seconds. The range setting is $10^{-11}$, the attenuation is 1, and the even temperature is 220° C. A Spectra-Physics "Minigrator" is used which records the data on a chart moving at 0.25 inch/minute. The benzyl alcohol peak height should be at least 1 inch. The gas chromatograph is calibrated by determining the ratio between the areas of the diethylene glycol and benzyl alcohol peaks for 2-aminoethanol solutions of diethylene glycol and benzyl alcohol in known proportions. A slope factor is calculated by dividing the ratio found into the known proportion.

The diethylene glycol/benzyl alcohol peak ratio is determined for the sample being analyzed. Then the mole percent diethylene glycol is equal to this ratio times the slope factor times 128.

We claim:

1. In the process of depolymerizing waste ethylene terephthalate polyester of form bis-(2-hydroxyethyl)-terephthalate and low molecular weight polymers thereof by glycolysis of the polyester waste with excess ethylene glycol at elevated temperatures; the improvement for inhibiting formation of glycol ethers which comprises preparing a reaction mixture of 1 part of the waste polyester in 0.88 to 3.6 parts bis-(2-hydroxyethyl)terephthalate, 0.1 to 0.5 part ethylene glycol and 0.000200 to 0.000500 part sodium acetate trihydrate, and heating the reaction mixture to depolymerize the polyester while continuously introducing 0.005 to 0.35 part per hour of water into the reaction mixture to inhibit formation of diethylene glycol.

* * * * *

UNITED STATES PATENT OFFICE
CERTIFICATE OF CORRECTION

PATENT NO. : 4,078,143
DATED : March 7, 1978
INVENTOR(S) : Abdul-Ilah Malik & Elmer Edwin Most It is certified that error appears in the above-identified patent and that said Letters Patent are hereby corrected as shown below:

Column 6, line 2, the word "of" should be -- to --.

Signed and Sealed this

Twenty-seventh Day of June 1978

[SEAL]

Attest:

RUTH C. MASON
*Attesting Officer*

DONALD W. BANNER
*Commissioner of Patents and Trademarks*